United States Patent [19]

Casadio et al.

[11] 3,952,108

[45] Apr. 20, 1976

[54] SCOPOLAMINE DERIVATIVES FOR TREATING ULCERS AND SPASMS

[75] Inventors: Silvano Casadio; Arturo Donetti, both of Milan, Italy

[73] Assignee: Istituto de Angeli S.p.A., Milan, Italy

[22] Filed: July 22, 1974

[21] Appl. No.: 490,266

Related U.S. Application Data

[62] Division of Ser. No. 350,927, April 13, 1973, Pat. No. 3,853,886.

[30] Foreign Application Priority Data

Apr. 18, 1972 United Kingdom............... 17920/72

[52] U.S. Cl................................. 424/265; 424/244; 424/247; 424/254; 424/260; 424/273; 424/311; 424/312

[51] Int. Cl.² ........................................ A61K 31/46

[58] Field of Search..................... 424/265, 256, 267

[56] References Cited

UNITED STATES PATENTS 3,847,924   11/1974   Tanaka et al.................. 424/265 X

*Primary Examiner*—Frederick E. Waddell
*Attorney, Agent, or Firm*—Stewart and Kolasch

[57] ABSTRACT

The specification describes quaternary bromides of scopolamine in which the substituent on the nitrogen atom has the formula $-(CH_2)_n-R$ in which R represents a cycloalkyl group containing up to six carbon atoms, an alkyl-substituted cycloalkyl group containing up to six carbon atoms or an epoxyethyl group and $n$ is 1 or 2. Such compounds have valuable spasmolytic and anti-ulcer properties and pharmaceutical preparations containing them are also described.

14 Claims, No Drawings

SCOPOLAMINE DERIVATIVES FOR TREATING ULCERS AND SPASMS

This application is a divisional of copendiing application Ser. No. 350,927, filed on Apr. 13, 1973, now U.S. Pat. NO. 3,853,886.

The present invention concerns new quaternary salts of scopolamine (the levo from of hyoscine) having valuable pharmacological properties.

The new compounds according to the invention have the general formula:

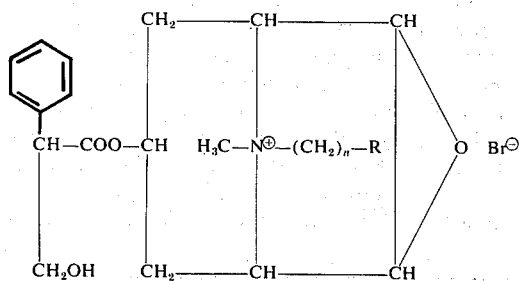

in which R represents a cycloalkyl, alkyl-substituted cycloalkyl or an epoxyethyl group, and $n$ is an integer which may be 1 or 2.

In compounds of formula (I) in which R is a cycloalkyl or an alkyl-substituted cycloalkyl group such groups may contain up to 6 carbon atoms and preferably are a cyclopropyl, cyclobutyl or a methyl-cyclopropyl group.

The new compounds according to the invention have valuable spasmolytic and anti-ulcer properties as shown in detail hereinafter.

According to another feature of the invention, there is further provided a process for the preparation of compounds of formula (I) which comprises reacting scopolamine, as the free base, with a bromide of formula:

$$R\text{-}(CH_2)_n\text{-}Br \qquad (II)$$

in which R is as above specified — to effect quaternization. The reaction is preferably carried out in a polar inert solvent or, if desired, in an excess of the bromide of formula (II) and at a temperature ranging from room temperature to the reflux temperature of the reaction medium, preferably between 40° and 100°C. It will be appreciated that the reaction time may vary depending on the solvent and the reaction temperature. Thus acetonitrile is advantageously used as a solvent, the temperature being kept at the reflux temperature of the reaction mixture.

According to a preferred manner of performing the reaction, 1 mole of scopolamine, free base, dissolved in acetonitrile, is refluxed with an excess of the bromide of formula (II) (from 1.1 to 2 moles), for a period from 10 to 100 hours. The quaternary salt so obtained may then be isolated by cooling the reaction mixture and filtering, by suction, the crystalline solid that separates or, if the quaternary salt is so soluble as not to crystallize from the reaction medium, by evaporating the solvent under reduced pressure, the residue so obtained being then dissolved in water, the solution filtered on charcoal, washed with ethyl ether and the solution evaporated to dryness and preferably lyophilized, to give the quaternary salt.

It will be appreciated that the main reaction may be accompanied by a side-reaction — namely dehydrohalogenation — which results in the formation of scopolamine hydrobromide so that the separation of the pure quaternary sale may be difficult.

We have now found that, in such cases, a pure product can be isolated in a practical and easy way by treating the reaction mixture with ethylene oxide, which reacts with scopolamine hydrobromide to give scopolamine free base and ethylene bromohydrin, both compounds being easily separable from the quaternary salt.

According to a preferred manner of effecting this purification, the reaction mixture, after completing the reaction, is cooled at room temperature, treated with an excess of ethylene oxide and left standing for 50–250 hours at 0–10°C. The solvent and the excess of ethylene oxide are then removed under reduced pressure and at a low temperature and the residue so obtained is dissolved in water, thoroughly washed with ether to remove the scopolamine base and the ethylene bromohydrin formed, and finally evaporated to dryness (preferably lyophilized.)

The compounds of formula (I) are colourless crystalline solids, when obtained by crystallization, or white amorphous solids, when obtained by lyophilization. They are soluble in water, methyl and ethyl alcohol, acetonitrile, dimethylformamide and practically insoluble in acetone, ether, dioxane and hydrocarbon solvents.

As stated above, the compounds according to the invention have valuable spasmolytic and anti-ulcer properties, coupled with a relatively low toxicity.

Preferred compounds for their useful properties are scopolamine-N-(cyclopropyl-methyl) bromide, scopolamine-N-(cyclobutyl-methyl) bromide, and scopolamine-N-(2-methyl-cyclopropyl-methyl)-bromide. A particularly preferred compound is scopolamine-N-(cyclopropyl-methyl)-bromide.

The properties of the new compounds may be illustrated by the results of the following experiments.

Acute toxicity

Acute toxicity in mice by intraperitoneal route. $LD_{50}$ have been calculated after 7 days of observation from the treatment according to Litchfield J. J. and Wilcoxon F., J. Pharm. Exp. Therm., 96, 99 (1949)

Spasmolytic activity

Spasmolytic activity on quinea pig ileum "in vitro" stimulated by acetylcholine ($1.10^{-7}$ g/ml) and by $BaCl_2$ ($1.10^{-4}$ g/ml) according to Turba C. and Marazzi-Uberti E., Arzneim Forsch. (Drug Res.) 16, 386, 391, (1966).

Spasmolytic activity on guinea pig gall-bladder "in vitro" stimulated by acetylcholine ($1.10^{-6}$ g/ml) according to Bertaccini G., De Caro G., Endean R., Ersparmer V. and Impicciatore M., Brit.J.Pharmacol., 34, 291–310 (1968).

Spasmolytic activity "in vivo" on rabbit choledochoduodenal junction stimulated by neostigmine (60 mcg/Kg i.v.), after i.v. administration of the compound under examination, according to Luoma P., Acta Pharmacol. e Toxicol., 29, suppl. 1, 5–55 (1971).

Anti-ulcer activity

Action on Shay ulcer in rats by intraduodenal route according to Shay H., Komarov S. A., Fels S. S., Meranze D., Gruenstein M. and Siplet H., Gastroenterology, 5, 43–61 (1945).

Action on gastric secretion in rats after intraduodenal administration according to Birnbaum G., Medicina Psicosomatica, 13, 1–4 (1968).

The above experiments have been carried out in comparison with scopolamine bromobutylate as a reference. The results are shown in the following table and are expressed on the basis of the activity of scopolamine bromobutylate being equal to 1.

corn, maize and soluble starches), talc and/or magnesium stearate.

Compositions for parenteral administration preferably consist of injectable solutions in a sterile carrier, preferably aqueous solutions. Such compositions are conveniently contained in vials.

In compositions for rectal administration the carrier is preferably a conventional suppository base, for example, a semi-synthetic glyceride.

The compositions are preferably formulated as dosage units adapted to supply a single dose of the active ingredient. Each dosage unit may conveniently contain from 1 to 100 mg and preferably from 2.5 to 25 mg of compound of formula (I).

As stated above, the pharmaceutical compositions according to the invention may contain other active ingredients in addition to the compound of formula (I). Particularly useful combination products include, for example, combination with analgesics (such as metamizole and d-propoxyphene), analgesic-sedatives (such as codeine salts and barbiturates), minor tranquilizers of the benzodiazepines class, anti-ulcer drugs (such as gefarnate), anti-emetics and anti-motion sickness drugs

| Pharmacological Tests | Dose mg/Kg | DA-3177 Scopolamine-N-(cyclo-propyl-methyl) bromide | DA-3235 Scopolamine-N-(2-methyl cyclopropyl-methyl)-bromide | DA-3236 Scopolamine-N-(cyclo-propyl-ethyl) bromide | DA-3237 Scopolamine-N-(cyclo-butyl-methyl) bromide | DA-3245 Scopolamine-N-(2,3-epoxy propyl)-bromide | Reference Scopolamine bromobutylate |
|---|---|---|---|---|---|---|---|
| Acute toxicity (in mice) | $LD_{50}$ i.p. | 0.6 | 0.8 | 1.3 | 0.8 | 0.7 | 1 |
| Spasmolytic activity on Guinea-pig ileum "in vitro" stimulated by: | | | | | | | |
| acetylcholine ($1.10^{-7}$) | $ED_{50}$ g/ml | 3.1 | 2.9 | 2.6 | 2.7 | 1.4 | 1 |
| $BaCl_2$ ($1.10^{-4}$) | $ED_{50}$ g/ml | 1.8 | 1.0 | 0.8 | 0.8 | 0.1 | 1 |
| Spasmolytic activity on Guinea-pig gall-bladder "in vitro" stimulated by: | | | | | | | |
| acetylcholine ($1.10^{-6}$) | $ED_{50}$ g/ml | 4.1 | 4 | 4.6 | 5.1 | 2.1 | 1 |
| Spasmolytic activity "in vivo" on rabbit choledochoduodenal junction stimulated by neostigmine (60 mcg/Kg i.v.): | | | | | | | |
| % increase of flux | 10mcg/Kg i.v. | 0.9 | 0.8 | 0.9 | 1.2 | 0.4 | 1 |
| Action on Shay ulcer in rats: | | | | | | | |
| % of animals protected from ulcer | 100 i.d. | 1.5 | 2 | 2 | 2 | 1.5 | 1 |
| Action on gastric secretion in rats: | | | | | | | |
| inhibition % of the gastric juice | 40 i.d. | 1 | 0.8 | 1.1 | 1.2 | 1.4 | 1 |

The above data show that the compounds of the invention have valuable spasmolytic and anti-ulcer properties, the spasmolytic properties mostly depending on their anti-cholinergic activity (inhibition of the action of acetylcholine). In particular DA-3177, DA-3235 and DA-3237, taking into account the relevant toxicities, have higher activities than the reference compound.

According to a further feature of the invention, there are also provided pharmaceutical compositions comprising one or more compounds of formula (I) — alone or in combination with other active ingredients — and suitable excipients or carriers. The compositions may be presented in forms suitable for oral, parenteral or rectal administration.

Thus, for example, compositions for oral administration may be tablets, dragees, pills or capsules. Suitable excipients include lactose, sugar, starches (particularly such as promethazine. The following examples are given merely as illustrative of the present invention and are not to be considered as limiting.

EXAMPLE 1

19.67 g (0.065 moles) of scopolamine base and 17.6 g (0.13 moles) of cyclopropyl-methyl-bromide are dissolved in acetonitrile and the solution is refluxed for 27 hours. After cooling the reaction mixture scopolamine-N-(cyclopropyl-methyl)-bromide crystallizes and, after filtering, it is recrystallized from acetonitrile (m.p. 174°C, $[\alpha]_D^{20°C, 3\% \ in \ H_2O} = -18.3°$ )

Analysis for $C_{21}H_{28}BrNO_4$: found % C, 57.46; H, 6.45; N, 3.24; Br, 18.28. calc % C, 57.54; H, 6.44; N, 3.19; Br, 18.23.

EXAMPLE 2

11.65 g (0.038 moles) of scopolamine base and 10.9 g (0.073 moles) of cyclopropyl-ethyl-bromide are dissolved in 100 ml of acetonitrile and the solution is refluxed for 99 hours. After cooling 4.82 g (0.11 moles) of ethylene oxide is added and then the reaction mixture is placed in an ice-box for 67 hours. After evaporating under reduced pressure the residue so obtained is dissolved in 150 ml of water and the solution is thoroughly washed with ether. The aqueous solution is lyophilized and scopolamine-N-(cyclopropyl-ethyl)-bromide is obtained. (m.p. 72°–75°C, $[\alpha]_D^{20(C,3\%\ in\ H_2O)} = -31.9°$)

Analysis for $C_{22}H_{30}BrNO_4$: found% C, 57.73; H, 6.73; N, 3.05; Br, 17.32. calc% C, 58.41; H, 6.68; N, 3.09; Br, 17.66.

The following quaternary salts are obtained in an analogous manner:

Scopolamine-N-(2-methyl-cyclopropyl-methyl)-bromide reaction time with ethylene oxide: 236 hours m.p. 76°–78°C, $[\alpha]_D^{20(C,3\%\ in\ H_2O)} = -12.8°$)

Analysis for $C_{22}H_{30}BrNO_4$: found% C, 57.70; H, 6.64; N, 3.08; Br, 17.76. calc% C, 58.41; H, 6.68; N, 3.09; Br, 17.66.

Scopolamine-N-(cyclobutyl-methyl)-bromide reaction time with ethylene oxide: 225 hours m.p. 76–78°C, $[\alpha]_D^{20(C,3\%\ in\ H_2O)} = -29.7°$ Analysis for $C_{22}H_{30}BrNO_4$: found% C, 57.85; H, 6.81; N, 3.02; Br, 17.41. calc% C, 58.41; H, 6.68; N, 3.09; Br, 17.66.

EXAMPLE 3

6.25 g (0.02 moles) of scopolamine base and 3.39 g. (0.024 moles) of epibromohydrin are dissolved in 55 ml of acetonitrile and the solution is refluxed for 15 hours. After evaporating acetonitrile under reduced pressure, the residue is dissolved in water. The solution is washed several times with ether and treated with charcoal. The aqueous solution is lyophilized and scopolamine-N-(2,3-epoxy propyl)-bromide is obtained (m.p. 73°–75°C), $[\alpha]_D^{20(C,3\%\ in\ H_2O)} = -7.4°$ Analysis for $C_{20}H_{26}BrNO_5$: found% C, 54.32; H, 6.03; N, 3.13; Br, 17.85. calc% C, 54.55; H, 5.95; N, 3.18; Br, 18.15.

EXAMPLE 4

Hard gelatine capsules

| | |
|---|---|
| Scopolamine-N-(cyclopropyl-methyl)-bromide | 10 mg |
| lactose | 89 mg |
| talc | 1 mg |

The ingredients are intimately mixed and pulverized, and the mixture is filled into hard gelatine capsules (0.100 g per capsule). Each capsule therefore contains 0.010 g of active substance.

EXAMPLE 5

Coated tablets

| | |
|---|---|
| Scopolamine-N-(cyclopropyl-methyl)-bromide | 10 mg |
| lactose, talc and sugar, corn starch q.s. to | 200 mg |

The active compound, the excipients and one half of the talc are intimately mixed. The mixture is compressed into pellets which are then granulated. The remaining talc is added to the granulate which is then compressed into tablets. The obtained tablets are coated with sugar and formed into coated tablets according to conventional techniques. Each coated tablet, containing 10 mg of active substance, weighs 200 mg.

EXAMPLE 6

Suppositories

| | |
|---|---|
| Scopolamine-N-(cyclopropyl-methyl)-bromide | 10 mg |
| semisynthetic glycerides q.s. to | 1200 mg |

The semisynthetic glycerides are melted and the active substance is dispersed in them, the mass obtained is filled into cold moulds to produce suppositories each of which weighs 1200 mg. each suppository contains 10 mg of active substance.

EXAMPLE 7

Vials

| | A | B |
|---|---|---|
| scopolamine-N-(cyclopropyl-methyl)-bromide | 10 mg | 20 mg |
| sodium chloride | 6 mg | 6 mg |
| distilled water q.s. to | 1 ml | 1 ml |

A solution of the active ingredient in distilled water is filtered through a sintered glass filter and then filled into vials of 1 ml or 5 ml volume. The vials are sterilized. Each vial contains 10 or 20 mg respectively of active substance.

EXAMPLE 8

Vials

| | | |
|---|---|---|
| scopolamine-N-(cyclopropyl-methyl)-bromide | 0.020 | g |
| sodium 1-phenyl-2,3-dimethyl-5-pyrazolone 4-methylaminomethane sulphonate (Novalgin") | 2.5 | g |
| distilled water q.s. to | 5 | ml |

The procedure is that of Example 7.

EXAMPLE 9

Suppositories

| | | |
|---|---|---|
| scopolamine-N-(cyclopropyl-methyl)-bromide | 0.010 | g |
| sodium 1-phenyl-2,3-dimethyl-5-pyrazolone-4-methylaminomethane sulphonate (Novalgin") | 1 | g |
| semisynthetic glycerides q.s. to | 2.8 | g |

The procedure is that of Example 6.

EXAMPLE 10

Coated tablets

| | |
|---|---|
| scopolamine-N-(cyclopropyl-methyl)-bromide | 0.010 g |
| sodium 1-phenyl-2,3-dimethyl-5-pyrazolone-4-methylaminomethane sulphonate (Novalgin") | 0.250 g |
| lactose, talc, sugar, corn starch q.s. to | 0.500 g |

The procedure is that of Example 5.

EXAMPLE 11

Coated tablets

| | |
|---|---|
| scopolamine-N-(cyclopropyl-methyl)-bromide | 10 mg |
| d-propoxyphene hydrochloride | 65 mg |
| corn starch, talc, sugar q.s. to lactose | 200 mg |

The procedure is that of Example 5.

EXAMPLE 12

Suppositories

|  | A | B |
|---|---|---|
| scopolamine-N-(cyclopropyl-methyl)-bromide | 10 mg | 7 mg |
| d-propoxyphene hydrochloride | 65 mg | 32.5 mg |
| semisynthetic glycerides q.s. to | 1.2 g | 1 g |

The procedure is that of Example 6.

EXAMPLE 13

Soft elastic capsules

|  | A | B |
|---|---|---|
| scopolamine-N-(cyclopropyl-methyl)-bromide | 5 mg | 10 mg |
| geranyl farnesylacetate | 50 mg | 100 mg |
| triglycerides of saturated vegetable fatty acids q.s. to | 100 mg | 200 mg |

The active ingredients are added to the triglycerides of saturated vegetable fatty acids and the solution is encapsulated in soft elastic capsules consisting of 45% gelatine, 20% glycerol and 35% water. The capsules obtained (0.155 g or 0.310 g per capsule) are then dried at room temperature. Each capsule contains 55 mg or 110 mg of active ingredients.

EXAMPLE 14

Coated tablets

|  | A | B |
|---|---|---|
| scopolamine-N-(cyclopropyl-methyl)-bromide | 10 mg | 5 mg |
| promethazine hydrochloride | 25 mg | 12.5 mg |
| corn starch, talc, sugar, q.s. to lactose | 200 mg | 150 mg |

The procedure is that of Example 5.

EXAMPLE 15

Suppositories

|  | A | B |
|---|---|---|
| scopolamine-N-(cyclopropyl-methyl)-bromide | 10 mg | 5 mg |
| promethazine hydrochloride | 25 mg | 12.5 mg |
| semisynthetic glycerides q.s. to | 1.2 g | 1 g |

The procedure is that of Example 6.

Compounds of the invention can be made up into pharmaceutical compositions and preparations by conventional techniques some of which are illustrated by Examples 4 to 15.

We claim:

1. A pharmaceutical composition useful for treating gastric ulcers or spasms which comprises an effective amount of at least one scopolamine derivative having the following general formula:

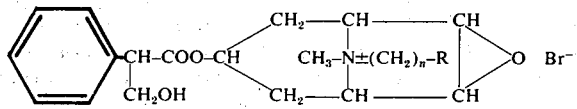

wherein R represents a cycloalkyl group containing up to five carbon atoms, a lower alkyl-substituted cycloalkyl group containing up to six carbon atoms or an epoxyethyl group and n is 1 or 2 and a solid pharmaceutically acceptable excipient or carrier.

2. The composition of claim 1 for oral administration, wherein the excipient comprises at least one member selected from the group consisting of lactose, a sugar starch, talc and magnesium stearate and the composition is in the form of a tablet, dragee, pill or capsule.

3. The composition of claim 1 for rectal administration, wherein the carrier is a semisynthetic glyceride and the composition is in the form of a suppository.

4. The composition of claim 1 additionally comprising an analgesic, an analgesic-sedative, a benzodiazepine tranquilizer, an anti-ulcer agent, an antiemetic or an anti-motion sickness agent.

5. The composition of claim 1 formulated as a dosage unit containing 1 to 100 mg. of the scopolamine compound defined in claim 1.

6. The composition of claim 5 wherein the dosage unit contains 2.5 to 25 mg. of said compound.

7. The composition of claim 1, wherein the pharmaceutically acceptable excipient or carrier is a sterile solution.

8. The composition of claim 1, wherein R is a cyclopropyl, cyclobutyl or a methyl-substituted cyclopropyl group.

9. The composition of claim 1, wherein the scopolamine derivative is scopolamine-N-(cyclopropylmethyl) bromide.

10. The composition of claim 1, wherein the scopolamine derivative is scopolamine-N-(2-methyl-cyclopropylmethyl) bromide.

11. The composition of claim 1, wherein the scopolamine derivative is scopolamine-N-(cyclopropylethyl) bromide.

12. The composition of claim 1, wherein the scopolamine derivative is scopolamine-N-(cyclobutylmethyl) bromide.

13. The composition of claim 1, wherein the scopolamine derivative is scopolamine-N-(2,3-epoxypropyl) bromide.

14. A method of treating gastric ulcers or spasms in a human being or an animal which comprises orally, parenterally or rectally administering to the human being or animal an effective spasmolytic or anti-ulcer amount of the scopolamine compound defined in claim 1.

* * * * *